US009635879B2

(12) United States Patent
Woodyer et al.

(10) Patent No.: US 9,635,879 B2
(45) Date of Patent: *May 2, 2017

(54) SWEETENER

(71) Applicant: Tate & Lyle Ingredients Americas LLC, Hoffman Estates, IL (US)

(72) Inventors: Ryan D. Woodyer, Hoffman Estates, IL (US); Jason C. Cohen, Hoffman Estates, IL (US); John R. Bridges, Hoffman Estates, IL (US)

(73) Assignee: TATE & LYLE INGREDIENTS AMERICAS LLC, Hoffman Estates, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/775,336

(22) PCT Filed: Mar. 14, 2014

(86) PCT No.: PCT/GB2014/050812
§ 371 (c)(1),
(2) Date: Sep. 11, 2015

(87) PCT Pub. No.: WO2014/140632
PCT Pub. Date: Sep. 18, 2014

(65) Prior Publication Data
US 2016/0021917 A1    Jan. 28, 2016

Related U.S. Application Data

(60) Provisional application No. 61/793,502, filed on Mar. 15, 2013.

(51) Int. Cl.
| A61K 47/00 | (2006.01) |
| A23L 27/30 | (2016.01) |
| A23L 2/60  | (2006.01) |
| A61K 8/60  | (2006.01) |
| A61Q 11/00 | (2006.01) |
| A61K 47/26 | (2006.01) |
| A61Q 19/00 | (2006.01) |
| A23P 20/10 | (2016.01) |
| A23L 29/30 | (2016.01) |

(52) U.S. Cl.
CPC .............. *A23L 27/33* (2016.08); *A23L 2/60* (2013.01); *A23L 27/37* (2016.08); *A23L 29/30* (2016.08); *A23P 20/10* (2016.08); *A61K 8/60* (2013.01); *A61K 47/26* (2013.01); *A61Q 11/00* (2013.01); *A61Q 19/00* (2013.01); *A23V 2002/00* (2013.01); *A23V 2200/00* (2013.01); *A23V 2200/16* (2013.01); *A61K 2800/5922* (2013.01)

(58) Field of Classification Search
CPC ................................................... A23L 1/2363
USPC ............................................................ 514/777
See application file for complete search history.

(56) References Cited

U.S. PATENT DOCUMENTS

| 4,570,029 | A   | 2/1986  | Kulprathipanja |         |
|-----------|-----|---------|----------------|---------|
| 4,692,514 | A   | 9/1987  | Chang          |         |
| 4,880,920 | A   | 11/1989 | Chang          |         |
| 5,286,499 | A   | 2/1994  | Courtright     |         |
| 5,411,880 | A   | 5/1995  | Izumori        |         |
| 5,679,562 | A   | 10/1997 | Izumori        |         |
| 6,051,236 | A   | 4/2000  | Portman        |         |
| 7,186,431 | B1  | 3/2007  | Silver         |         |
| 8,012,940 | B2  | 9/2011  | Nagata         |         |
| 8,030,035 | B2  | 10/2011 | Oh             |         |
| 8,216,818 | B2  | 7/2012  | Maruta         |         |
| 8,383,183 | B2  | 2/2013  | Prakash        |         |
| 8,420,606 | B2  | 4/2013  | Izumori        |         |
| 9,049,876 | B2* | 6/2015  | Fujihara       | A23L 1/09 |
| 2002/0197352 | A1 | 12/2002 | Portman   |         |
| 2003/0064135 | A1 | 4/2003  | Portman   |         |
| 2004/0143024 | A1 | 7/2004  | Yoshino   |         |
| 2005/0013915 | A1 | 1/2005  | Riha      |         |
| 2005/0037121 | A1 | 2/2005  | Rathjen   |         |
| 2005/0095271 | A1 | 5/2005  | Mathewson |         |
| 2005/0245459 | A1 | 11/2005 | Izumori   |         |
| 2007/0020358 | A1 | 1/2007  | Mower     |         |

(Continued)

FOREIGN PATENT DOCUMENTS

| AU | 2011203233 | 7/2011 |
| CA | 1266834    | 3/1990 |

(Continued)

OTHER PUBLICATIONS

Non Final Office Action mailed Feb. 2, 2016 for U.S. Appl. No. 14/212,152.

Zijie et al., "Enzymatic Synthesis of D-Sorbose and D-Psicose with Aldolase RhaD; Effect of Acceptor Configuration on Enzyme Stereoselectivity", Bioorg Med Chem Lett. Dec. 1, 2011; 21(23) pp. 7081-7084.

Keith et al., "Discrimination tests: Evaluating context effects and respondent reliability using the switchback experimental design", Journal of Targeting, Measurement and Analysis for Marketing (2009) 17, pp. 115-125.

Nabors, Alternative Sweeteners, 3rd Edition, New York: Marcel Dekker Inc., 2001, pp. 335-338, 352-353, 367-371, 373-374.

(Continued)

*Primary Examiner* — Nizal Chandrakumar
(74) *Attorney, Agent, or Firm* — RatnerPrestia

(57) ABSTRACT

A low calorie sweetener composition with sweetness synergy, providing a reduction in off-taste and a desirable temporal profile. The sweetener composition comprises allulose, fructose and sucralose. In a preferred embodiment, the sweetener composition comprises allulose in an amount of at least about 45%, fructose in an amount of at least about 20%, and sucralose in an amount of at least about 0.01% by weight relative to the total weight of allulose, fructose and sucralose in the composition. The sweetener composition is suitable for use as a substitute for high calorie sugars. The sweetener composition is for use in food and beverage products, pharmaceutical products, nutritional product and cosmetic products.

22 Claims, 1 Drawing Sheet

(56) References Cited

U.S. PATENT DOCUMENTS

| | | | |
|---|---|---|---|
| 2007/0116823 A1 | 5/2007 | Prakash | |
| 2008/0221044 A1 | 9/2008 | Tokuda | |
| 2008/0260925 A1 | 10/2008 | Zink | |
| 2008/0292765 A1 | 11/2008 | Prakash | |
| 2009/0068710 A1 | 3/2009 | Izumori | |
| 2009/0304891 A1* | 12/2009 | Fujihara | A23C 9/13 426/548 |
| 2010/0129865 A1 | 5/2010 | Maruta | |
| 2010/0130435 A1 | 5/2010 | Tokuda | |
| 2010/0166678 A1 | 7/2010 | Iida | |
| 2010/0204346 A1 | 8/2010 | Okuma | |
| 2010/0222284 A1 | 9/2010 | Tokuda | |
| 2010/0285195 A1 | 11/2010 | Fisher | |
| 2010/0285197 A1 | 11/2010 | Fisher | |
| 2011/0112043 A1 | 5/2011 | Izumori | |
| 2011/0160311 A1 | 6/2011 | Prakash | |
| 2011/0237790 A1 | 9/2011 | Lee | |
| 2011/0275138 A1 | 11/2011 | Maruta | |
| 2011/0318464 A1 | 12/2011 | Prakash | |
| 2012/0070534 A1 | 3/2012 | Suzuki | |
| 2012/0076893 A1 | 3/2012 | Asayama | |
| 2012/0076908 A1 | 3/2012 | Fujihara | |
| 2012/0094940 A1 | 4/2012 | Takamine | |
| 2012/0244580 A1 | 9/2012 | Hung | |
| 2013/0012459 A1 | 1/2013 | Tokuda | |
| 2013/0136838 A1 | 5/2013 | SanMiguel | |
| 2014/0037814 A1 | 2/2014 | Quinlan | |
| 2014/0087049 A1 | 3/2014 | Ankolekar | |
| 2014/0272068 A1 | 9/2014 | Prakash | |

FOREIGN PATENT DOCUMENTS

| | | |
|---|---|---|
| CA | 1292988 | 12/1991 |
| CN | 102876817 | 1/2013 |
| EP | 1864669 | 12/2007 |
| EP | 2098227 | 9/2009 |
| EP | 2156751 | 2/2010 |
| EP | 2537422 | 12/2012 |
| EP | 2548453 | 1/2013 |
| JP | 200111090 | 1/2001 |
| JP | 2001354690 | 12/2001 |
| JP | 2005213227 | 11/2005 |
| JP | 200843342 | 2/2008 |
| JP | 200848685 | 3/2008 |
| JP | 2010018528 | 1/2010 |
| JP | 2010178683 | 8/2010 |
| JP | 4724824 | 7/2011 |
| JP | 4761424 | 8/2011 |
| JP | 2011205913 | 10/2011 |
| JP | 2013138660 | 7/2013 |
| JP | 5308585 | 10/2013 |
| JP | 5314207 | 10/2013 |
| KR | 100832339 | 5/2008 |
| KR | 20110041910 | 4/2011 |
| KR | 1020110041910 | 4/2011 |
| KR | 101106253 | 1/2012 |
| WO | 9418855 | 9/1994 |
| WO | 9930577 | 6/1999 |
| WO | 2007010975 | 1/2007 |
| WO | 2007010976 | 1/2007 |
| WO | 2008059625 | 5/2008 |
| WO | 2008102137 | 8/2008 |
| WO | 2011040708 | 4/2011 |
| WO | 2011139959 | 11/2011 |
| WO | 2013036768 | 3/2013 |
| WO | 2013039365 | 3/2013 |
| WO | 2013081294 | 6/2013 |
| WO | 2014025235 | 2/2014 |

OTHER PUBLICATIONS

Wiet et al., "Sensory Characteristics of Sucralose and other High Intensity Sweeteners", Journal of Food Science, vol. 57, No. 4, 1992, pp. 1014-1019.

Definition of "buttercream" from Merriam Webster On-Line Dictionary, downloaded Dec. 1, 2015 from http://www.merriam-webster.com/dictionary/buttercream.

Angyal; The Lobry de Bruyn-Alberda van Ekenstein Transformation and Related Reactions; Topics in Current Chemistry, vol. 215, pp. 1-14.

Bruijn, et al.; Alkaline Degradation of Monosaccharides V*: Kinetics of the Alkaline Isomerization and Degradation of Monosaccharides; Recueil des Travaux Chimiques des Pays-Bas, 106/2, Feb. 1987, pp. 35-43.

Combined Search and Examination Report dated Aug. 21, 2014 for GB Application No. 1403030.8, 8 pgs.

Combined Search and Examination Report issued for Application No. GB 1309076.6 dated Nov. 15, 2013.

Combined Search and Examination Report Issued for Application No. GB 1309077.4 Dated Nov. 15, 2013.

Combined Search and Examination Report issued for Application No. GB 1309079.0 dated Nov. 15, 2013.

Doner; Isomerization of D-Fructose by Base: Liquid-Chromatographic Evaluation and the Isolation of D-Psicose; Carbohydrate Research, 70 (1979)209-216, Elsevier Scientific Publishing Company.

Entire patent prosecution history of U.S. Appl. No. 14/777,047, filed Sep. 15, 2015, entitled, "Improved Sweetener."

Entire patent prosecution history of U.S. Appl. No. 14/777,157, filed Sep. 15, 2015, entitled, "Improved Sweetener."

Entire patent prosecution history of U.S. Appl. No. 14/212,152, filed Mar. 14, 2014, entitled, "Sweetener."

Entire patent prosecution history of U.S. Appl. No. 14/212,178, filed Mar. 14, 2014, entitled, "Sweetener."

Entire patent prosecution history of U.S. Appl. No. 14/212,196, filed Mar. 14, 2014, entitled, "Sweetener."

Final Office Action mailed May 21, 2015 in U.S. Appl. No. 14/212,178.

Matsuo, et al.; D-Psicose Is a Rare Sugar That Provides No Energy to Growing Rats; J. Nutr. Sci. Vitaminol, 48, 77-80, 2002.

Matsuo, et al.; Dietary D-psicose, a C-3 epimer of D-fructose, suppresses the activity of hepatic lipogenic enzymes in rats; Asia Pacific J. Clin. Nutr. (2001) 10 (3): 233-237.

Notification of Transmittal of International Search Report and the Written Opinion of the International Searching Authority, or the Declaration Issued for International Application No. PCT/GB2014/050812, Completed May 13, 2014 and mailed May 23, 2014.

Notification of Transmittal of the International Search Report and the Written Opinion of the International Searching Authority, or the Declaration Issued for International Application No. PCT/GB2014/050813, Completed May 14, 2014 and Mailed May 23, 2014.

Notification of Transmittal of the International Search Report and the Written Opinion of the International Searching Authority, or the Declaration issued for International Application No. PCT/GB2014/050814, Completed May 14, 2014 and mailed Jun. 23, 2014.

Final Office Action for U.S. Appl. No. 14/212,196, mailed Jun. 16, 2016, 25 pages.

Hemback, J., "Determination of the GRAS Status of the Use of Luo Han Fruit Concentrate as Flavor Modifier and Sweetener," Jul. 2009, 110 pages.

Wang, et al., "Cucurbitane Glycosides Derived from Mogroside IIE: Structure-Taste Relationships, Antioxidant Activity, and Acute toxicity,", Molecules, 2014, vol. 19, pp. 12676-12689.

Non-Final Office Action mailed Oct. 16, 2015 in U.S. Appl. No. 14/212,196.

International Preliminary Report on Patentability for International Application No. PCT/GB2014/050812 mailed Sep. 15, 2015.

International Preliminary Report on Patentability for International Application No. PCT/GB2014/050813 mailed Sep. 15, 2015.

International Preliminary Report on Patentability for International Application No. PCT/GB2014/050814 mailed Sep. 15, 2015.

Wang et al., "Crystalline fructose features and industrial production", Polysaccharide Drug Research and Application of Chinese Medicine Institute Symposium Proceedings, Jul. 2008, 17 pages (with translation).

Chinese Office Action for Chinese Application No. 201480014834.6, dated Sep. 26, 2016 with translation, 18 pages.

* cited by examiner

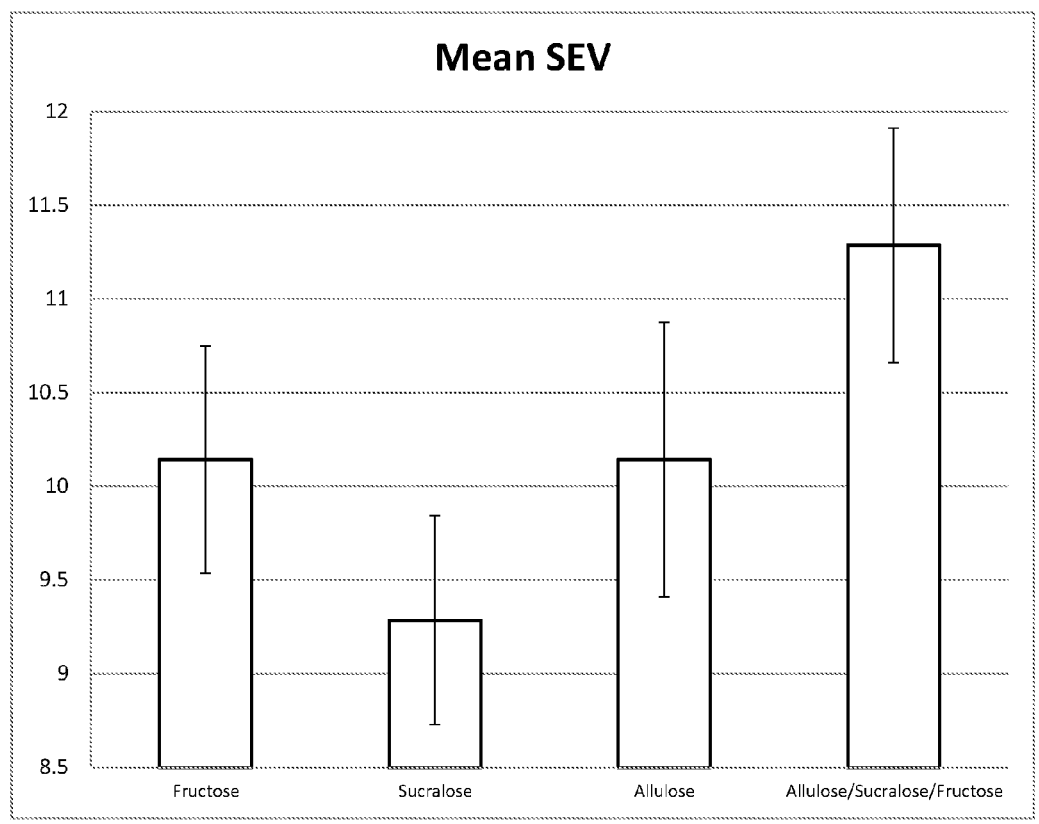

SWEETENER

CROSS-REFERENCE TO RELATED APPLICATIONS

This is the national phase of International Application No. PCT/GB2014/050812, filed Mar. 14, 2014, which claims priority to U.S. Provisional Application No. 61/793,502, filed Mar. 15, 2013. The disclosures of both of these applications are incorporated herein by reference in their entirety for all purposes.

FIELD OF THE INVENTION

The present invention relates to a low calorie sweetener composition having sweetness synergy. The present invention also relates to food or beverage products comprising said sweetener composition.

BACKGROUND OF THE INVENTION

Many food and beverage products contain nutritive sweeteners such as sucrose (generally referred to as 'sugar' or 'table sugar'), glucose, fructose, corn syrup, high fructose corn syrup and the like. Such sweeteners supply not only sweetness to the food and beverage products, but also bulk, texture and desirable functional properties such as browning, humectancy, freezing point depression and the like. They also produce a favorable sensory response, for example in terms of quality of sweetness, lack of bitterness and off taste, desirable temporal profile and desirable mouthfeel.

Although desirable in terms of taste and functional properties, excess intake of nutritive sweeteners, such as sucrose, has long been associated with an increase in diet-related health issues, such as obesity, heart disease, metabolic disorders and dental problems. This worrying trend has caused consumers to become increasingly aware of the importance of adopting a healthier lifestyle and reducing the level of nutritive sweeteners in their diet.

In recent years, there has been a movement towards the development of replacements for nutritive sweeteners, with a particular focus on the development of low or zero-calorie sweeteners. An ideal replacement for a nutritive sweetener is a sweetener that has the same desirable taste characteristics and functional properties as the nutritive sweetener, but which also has fewer calories. Aiming to meet this growing need, the market has been flooded with possible candidates to replace conventional nutritive sweeteners. Unfortunately, however, many of the low or zero calorie replacements offered on the market lack one or all of the necessary characteristics, and often exhibit bitterness or off-taste. Therefore, many of the proposed sweeteners are not an ideal replacement for nutritive sweeteners.

One proposed alternative to nutritive sweeteners is allulose (also known as D-psicose). Allulose is known as a "rare sugar", since it occurs in nature in only very small amounts. It provides around 70% of the sweetness of sucrose, but only around 5% of the calories (approximately 0.2 kcal/g). It may therefore essentially be considered to be a 'zero calorie' sweetener.

In view of its scarcity in nature, production of allulose relies on the epimerization of readily available fructose. Ketose-3-epimerases can interconvert fructose and allulose, and various ketose-3-epimerases are known for carrying out this conversion.

U.S. Pat. No. 8,030,035 and PCT publication no. WO2011/040708 disclose that D-psicose (an alternative name for allulose) can be produced by reacting D-fructose with a protein derived from *Agrobacterium tumefaciens*, and having psicose 3-epimerase activity.

US patent publication no. 2011/0275138 discloses a ketose 3-epimerase derived from a microorganism of the *Rhizobium* genus. This protein shows a high specificity to D- or L-ketopentose and D- or L-ketohexose, and especially to D-fructose and D-psicose. This document also discloses a process for producing ketoses by using the protein.

Korean patent no. 100832339 discloses a Sinorhizobium YB-58 strain which is capable of converting fructose into psicose (i.e. allulose), and a method of producing psicose using a fungus body of the Sinorhizobium YB-58 strain.

Korean patent application no. 1020090098938 discloses a method of producing psicose using *E. coli* wherein the *E. coli* expresses a polynucleotide encoding a psicose 3-epimerase.

Allulose is present in processed cane and beet molasses, steam-treated coffee, wheat plant products and high fructose corn syrup. D-allulose is the C-3 epimer of D-fructose and the structural differences between allulose and fructose result in allulose not being metabolized by the human body to any significant extent, and thus having "zero" calories. Thus, allulose is thought to be a promising candidate as a replacement for nutritive sweeteners and as a sweet bulking agent, as it has no calories and is reported to be sweet while maintaining similar properties to sucrose. However, the use of allulose alone as a replacement for nutritive sweeteners may have some limitations due to cost and digestive tolerance in some applications.

Alternative sweeteners on the market include sucralose and fructose. Sucralose is a 'high potency' or 'high intensity' sweetener that is approximately 600 times as sweet as sucrose. Fructose (also known as "fruit sugar") is a 6-carbon polyhydroxyketone monosaccharide sugar that is often found in plants and in honey. The monosaccharide is found in crystalline form, often referred to as D-fructose. Fructose can also be found as a component of other sweeteners such as high-fructose corn syrup (HFCS), which is a mixture of glucose and fructose. Fructose is frequently used to enhance the sweetness and taste of food and beverage products. Using fructose as a replacement for sucrose and other nutritive sweeteners also has its limitations, as fructose is fully caloric and thus does not provide an effective calorie reduction strategy.

Therefore, there is a need to provide an improved replacement for nutritive sweeteners that has low calories and is without limitations in use, but which also has taste characteristics and functional properties similar to those of sucrose and other nutritive sweeteners.

The present invention seeks to provide a solution to the above-mentioned problem by providing a sweetener composition having taste characteristics comparable to sucrose but having low calories. Advantageously, the present invention also seeks to provide a sweetener composition having sweetness synergy, a reduction in off-taste or off-flavor, a desirable temporal profile and improved mouthfeel, compared with proposed sweeteners currently available on the market.

SUMMARY OF THE INVENTION

A first aspect of the present invention provides a sweetener composition comprising allulose, fructose and sucralose.

Preferably, the sweetener composition comprises allulose in an amount of at least about 45%, fructose in an amount of at least about 20%, and sucralose in an amount of at least about 0.01% by weight relative to the total weight of allulose, fructose and sucralose in the composition.

According to one embodiment, the sweetener composition comprises allulose in an amount of about 45% to about 80%, fructose in an amount of about 20% to about 55%, and sucralose in an amount of about 0.01% to about 0.3% by weight relative to the total weight of allulose, fructose and sucralose in the composition.

According to another embodiment, the sweetener composition comprises allulose in an amount of about 45% to about 80%, fructose in an amount of about 20% to about 55%, and sucralose in an amount of about 0.02% to about 0.3% by weight relative to the total weight of allulose, fructose and sucralose in the composition.

According to another embodiment, the sweetener composition comprises allulose in an amount of about 55% to about 70%, fructose in an amount of about 30% to about 45%, and sucralose in an amount of about 0.1% to about 0.25% by weight relative to the total weight of allulose, fructose and sucralose in the composition.

According to another embodiment, the sweetener composition comprises allulose in an amount of about 65% to about 75%, fructose in an amount of about 25% to about 35%, and sucralose in an amount of about 0.01% to about 0.06% by weight relative to the total weight of allulose, fructose and sucralose in the composition.

According to another embodiment, the sweetener composition comprises allulose in an amount of about 70% to about 80%, fructose in an amount of about 20% to about 30%, and sucralose in an amount of about 0.02% to about 0.1% by weight relative to the total weight of allulose, fructose and sucralose in the composition.

According to another embodiment, the sweetener composition comprises allulose in an amount of about 45% to about 55%, fructose in an amount of about 45% to about 55%, and sucralose in an amount of about 0.02% to about 0.1% by weight relative to the total weight of allulose, fructose and sucralose in the composition.

According to another embodiment, the sweetener composition comprises allulose in an amount of about 62%, fructose in an amount of about 38%, and sucralose in an amount of about 0.2% by weight relative to the total weight of allulose, fructose and sucralose in the composition.

According to another embodiment, the sweetener composition comprises allulose in an amount of about 77%, fructose in an amount of about 23%, and sucralose in an amount of about 0.05% by weight relative to the total weight of allulose, fructose and sucralose in the composition.

According to another embodiment, the sweetener composition comprises allulose in an amount of about 46%, fructose in an amount of about 54%, and sucralose in an amount of about 0.06% by weight relative to the total weight of allulose, fructose and sucralose in the composition.

According to another embodiment, the sweetener composition comprises allulose in an amount of about 68%, fructose in an amount of about 32%, and sucralose in an amount of about 0.03% by weight relative to the total weight of allulose, fructose and sucralose in the composition.

In some embodiments, the sweetener composition further comprises a sweet taste improving additive, a bulking agent, a flavoring agent, and/or a stabilizer.

A further aspect of the present invention provides a food or beverage product comprising the sweetener composition of the invention.

According to one embodiment, the food or beverage product comprises allulose, fructose and sucralose in a total amount of about 2% to about 12% by weight based on the total weight of the food or beverage product.

According to another embodiment, the food or beverage product comprises allulose, fructose and sucralose in a total amount of about 2% to about 5% by weight based on the total weight of the food or beverage product.

According to another embodiment, the food or beverage product comprises allulose, fructose and sucralose in a total amount of about 4% to about 10% by weight based on the total weight of the food or beverage product.

According to another embodiment, the food or beverage product comprises allulose, fructose and sucralose in a total amount of about 6% to about 12% by weight based on the total weight of the food or beverage product.

According to one embodiment, the food or beverage product is a food product and the sweetener composition is provided as a coating or frosting on the surface of the food product. According to another embodiment, the product is a carbonated or non-carbonated beverage.

A further aspect of the present invention provides a table-top sweetener comprising the sweetener composition of the invention.

Further aspects of the present invention provide: a bulking agent comprising the sweetener composition of the invention; a coating agent comprising the sweetener composition of the invention; a cosmetic product comprising the sweetener composition of the invention; a pharmaceutical product comprising the sweetener composition of the invention; a nutritional product comprising the sweetener composition of the invention; and a sports product comprising the sweetener composition of the invention.

Another aspect of the present invention provides the use of the sweetener composition according to the present invention in a food product, a beverage product, a pharmaceutical product, a nutritional product, a sports product, or a cosmetic product. Another aspect of the present invention provides the use of the sweetener composition according to the present invention as a bulking agent. Another aspect of the present invention provides the use of the sweetener composition according to the present invention as a coating agent.

DETAILED DESCRIPTION OF THE FIGURES

FIG. 1: Graph illustrating the Mean SEV for allulose, fructose, sucralose and a composition comprising allulose, fructose and sucralose.

DETAILED DESCRIPTION OF THE INVENTION

The present invention is based on the surprising finding that allulose, fructose and sucralose exhibit sweetness synergy, whereby the blend is sweeter than the expected sweetness based on the sweetness of its components. That is to say, the relative sweetness of the sweetener composition is greater than the sweetness calculated from the individual components of the composition.

Furthermore, it has been found that this blend of allulose, fructose and sucralose addresses problems associated with the individual components, in particular, with regard to off-flavor and/or undesirable temporal profile. In addition, due to the presence of the zero calorie sweeteners, allulose and sucralose, the sweetener composition is low calorie. Furthermore, as a consequence of the sweetness synergy exhibited by the composition, the amount of the composition required to provide a given level of sweetness is less than would be expected in the absence of synergy, thereby allowing a further reduction in calories. Thus, the sweetener composition of the present invention provides enhanced sweetness, improves the balance of flavor by reducing off-taste or off-flavor, and provides a more desirable temporal profile, while at the same time allowing a significant reduction in calories compared to a sweet-equivalent amount of a conventional nutritive sweetener.

Using the sweetener composition of the present invention allows delivery of an increased sweetness in food or beverage products when compared to the individual components used separately. This enhanced sweetness means that a smaller amount of sweetener can be used in these products, to provide a temporal and taste profile that closely matches that of sucrose.

In general terms, the present invention relates to a sweetener composition comprising the sweeteners allulose, fructose and sucralose.

The term "allulose" as used herein refers to a monosaccharide sugar of the structure shown as a Fischer projection in below Formula I. It is also known as "D-psicose":

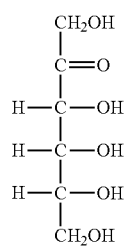

Formula (I)

The term "fructose" as used herein refers to the monosaccharide sugar of the structure shown as a Fischer projection in below Formula II:

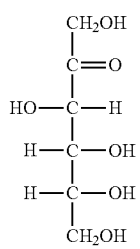

Formula (II)

The term "sucralose" as used herein refers to sucralose of the structure shown in Formula III:

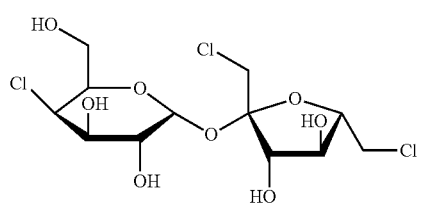

Formula (III)

The term "temporal profile" of a composition, sugar or sweetener, as used herein, is a measure of the perceived sweetness intensity of said composition, sugar or sweetener over time. A desirable or advantageous temporal profile is one wherein sweetness is observed quickly and has a short linger similar to that of sucrose.

The term "sucrose equivalent value" or "SEV" as used herein refers to the sweetness equivalent of a sweetener related to the sweetness of sucrose. For example, a sweetener at an SEV value of 5 would have a sweetness similar to a 5% by weight solution of sucrose.

The term "low calorie" as used herein refers to a sweetener having 40 calories or fewer per reference amount customarily consumed (RACC) and per labeled serving.

All amounts given in % by weight are quoted on a dry solids (ds) basis unless specifically stated otherwise. Thus, where components are provided other than in their pure form, the amount added should be adjusted to provide the required amount on a dry solids basis. For example, where allulose is provided as a syrup, the amount of syrup used should be adjusted to supply the required amount of allulose on a dry solids basis.

The present invention provides a sweetener composition comprising allulose, fructose and sucralose.

According to an embodiment of the invention, the sweetener composition consists essentially of allulose, fructose and sucralose. According to another embodiment, the sweetener composition consists of allulose, fructose and sucralose.

According to one embodiment of the present invention, the sweetener composition comprises allulose in an amount of at least about 45%, fructose in an amount of at least about 20%, and sucralose in an amount of at least about 0.01% by weight relative to the total weight of allulose, fructose and sucralose in the composition.

In another embodiment of the present invention, the sweetener composition comprises allulose in an amount of about 45% to about 80%, fructose in an amount of about 20% to about 55%, and sucralose in an amount of about 0.01% to about 0.3% by weight relative to the total weight of allulose, fructose and sucralose in the composition.

In another embodiment of the present invention, the sweetener composition comprises allulose in an amount of about 45% to about 80%, fructose in an amount of about 20% to about 55%, and sucralose in an amount of about 0.02% to about 0.3% by weight relative to the total weight of the composition, preferably relative to the total weight of allulose, fructose and sucralose in the composition.

Preferably, the sweetener composition of the invention comprises allulose in an amount of about 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79% or 80%, fructose in an amount of about 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54% or 55%, and sucralose in an amount of about 0.01%, 0.02%, 0.03%, 0.04%, 0.05%, 0.06%, 0.07%, 0.08%, 0.09%, 0.10%, 0.11%, 0.12%, 0.13%, 0.14%, 0.15%, 0.16%, 0.17%, 0.18%, 0.19%, 0.20%, 0.21%, 0.22%, 0.23%, 0.24%, 0.25%, 0.26%, 0.27%, 0.28%, 0.29%, or 0.30%, by weight relative to the total weight of the composition, preferably relative to the total weight of allulose, fructose and sucralose in the composition.

It is particularly preferred that the sweetener composition comprises allulose in an amount of about 62% (for example about 61.4%), preferably about 55% to about 70%, or about 60% to about 63%, or about 60% to about 64%; fructose in an amount of about 38% (for example about 38.4%), preferably about 30% to about 45%, or about 36% to about 40%, or about 37% to about 40%; and sucralose in an amount of about 0.2%, preferably about 0.1% to about 0.25%, or about 0.18% to about 0.22% by weight relative to the total weight of the composition, preferably relative to the total weight of allulose, fructose and sucralose in the composition. In a another preferred embodiment of the present invention, the sweetener composition comprises allulose in an amount of about 77% (for example about 77.4%), preferably about 70% to about 85%, or about 70% to about 80%, or about 75% to about 79%, or about 76% to about 80%; fructose in an amount of about 23% (for example about 22.5%), preferably about 15% to about 30%, or about 20% to about 30%, or about 21% to about 25%, or about 20% to about 24%; and sucralose in an amount of about 0.05%, preferably about 0.02% to about 0.1%, or about 0.03% to about 0.07% by weight relative to the total weight of the composition, preferably relative to the total weight of allulose, fructose and sucralose in the composition. In an alternative embodiment of the present invention, the sweetener composition comprises allulose in an amount of about 46% (for example about 46.1%), preferably about 40% to about 55%, or about 45% to about 55%, or about 42% to about 49%, or about 45% to about 48%; fructose in an amount of about 54% (for example about 53.8%), preferably about 45% to about 60%, or about 45% to about 55%, or about 51% to about 58%, or about 52% to about 55%; and sucralose in an amount of about 0.06%, preferably, about 0.02% to about 0.1%, or about 0.04% to about 0.08% by weight relative to the total weight of the composition, preferably relative to the total weight of allulose, fructose and sucralose in the composition. In another embodiment of the present invention, the sweetener composition comprises allulose in an amount of about 68%, fructose in an amount of about 32%, and sucralose in an amount of about 0.03% by weight relative to the total weight of the composition, preferably relative to the total weight of allulose, fructose and sucralose in the composition.

In a preferred embodiment of the present invention, each component of the sweetener composition, i.e. each of allulose, fructose and sucralose, is provided in an amount of at least 25% by percentage of added sweetness in terms of relative sugar equivalent value (SEV).

In another embodiment of the present invention, two of the components of the sweetener composition, selected from allulose, fructose and sucralose, are present in an amount of about 25% (by percentage of added sweetness in terms of relative sugar equivalent value (SEV)) and the remaining component is present in an amount of about 50% (by percentage of added sweetness in terms of relative sugar equivalent value (SEV)).

Advantageously, the sweetener composition comprises allulose in an amount of about 25%, fructose in an amount of about 25%, and sucralose in an amount of about 50% (by percentage of added sweetness in terms of relative sugar equivalent value (SEV)). In an alternative embodiment, the sweetener composition comprises allulose in an amount of about 50%, fructose in an amount of about 25% and sucralose in an amount of about 25% (by percentage of added sweetness in terms of relative sugar equivalent value (SEV)). The sweetener may, alternatively, comprise allulose in an amount of about 25%, fructose in an amount of about 50% and sucralose in an amount of about 25% (by percentage of added sweetness in terms of relative sugar equivalent value (SEV)).

In some embodiments, the sweetener composition may further comprise a sweet taste improving additive, a bulking agent, a flavoring agent, and/or a stabilizer.

A further aspect of the present invention provides a food product comprising the sweetener composition of the invention. Non-limiting examples of a food product include a confectionery product (including, but not limited to, jelly candies, hard candies and gums), a dessert product such as yogurt (including, but not limited to, full fat, reduced fat and fat-free dairy yoghurts, as well non-dairy and lactose-free yoghurts and frozen equivalents of all of these), frozen desserts (including, but not limited to, frozen dairy desserts such as ice-cream—including regular ice cream, soft-serve ice cream and all other types of ice cream—and frozen non-dairy desserts such as non-dairy ice cream, sorbet and the like), sweet bakery products (including, but not limited to, biscuits, cakes, rolls, pies, pastries, and cookies), pre-made sweet bakery mixes for preparing sweet bakery products, pie fillings (including, but not limited to, fruit pie fillings and nut pie fillings such as pecan pie filling), a cereal product such as sweetened breakfast cereals (including, but not limited to, extruded (kix type) breakfast cereals, flaked breakfast cereals and puffed breakfast cereals), cereal coating compositions, baked goods including bread products (including, but not limited to, leavened and unleavened breads, yeasted and unyeasted breads such as soda breads, breads comprising any type of wheat flour, breads comprising any type of non-wheat flour (such as potato, rice and rye flours), gluten-free breads), pre-made bread mixes for preparing bread products, frozen dairy products, meats, dairy products, condiments, snack bars (including, but not limited to, cereal, nut, seed and/or fruit bars), soups, dressings, mixes, prepared foods, baby foods, diet preparations, syrups, food coatings, dried fruit, sauces, gravies, spreads (including, but not limited to, jams/jellies butters and other spreadable preserves, conserves and the like). Other types of food product not mentioned here but which conventionally include one or more nutritive sweetener may also be contemplated in the context of the present invention, especially those which are reduced sugar or low sugar products. The food product may be an animal feed product. The food product of the invention may comprise the sweetener composition as a coating or frosting formed on the surface of the product. This coating improves the flavor of the food product as well as its shelf life.

Another aspect of the invention provides a beverage product comprising the sweetener composition of the present invention. Non-limiting examples of a beverage product include a carbonated beverage (including, but not limited to, soft carbonated beverages), a non-carbonated beverage (including, but not limited to, soft non-carbonated beverages such as flavored waters and sweet tea or coffee based beverages), fruit-flavored beverage, fruit-juice, tea, milk, coffee, especially those which are reduced sugar or low sugar products. Other types of beverage product not mentioned here but which conventionally include one or more nutritive sweetener may also be contemplated in the context of the present invention, especially those which are reduced sugar or low sugar products.

A further aspect of the present invention provides a table-top sweetener comprising the sweetener composition of the invention.

Another aspect of the present invention provides a bulking agent comprising the sweetener composition of the invention.

Another aspect of the present invention provides a coating agent comprising the sweetener composition of the invention.

Another aspect of the present invention provides a pharmaceutical product comprising the sweetener composition of the invention.

Another aspect of the present invention provides a nutritional or sports product comprising the sweetener composition of the invention.

Another aspect of the present invention provides a cosmetic product comprising the sweetener composition of the invention.

It will be appreciated that the amount of the sweetener composition of the invention present in a food product, a beverage product, a pharmaceutical product, a nutritional product, a sports product, or a cosmetic product, will depend upon the type and amount of sweetener present in the sweetener composition and the desired sweetness of the food or beverage product.

In one embodiment, the food or beverage product comprises the sweetener composition in an amount such that the food or beverage product contains allulose, fructose and sucralose in a total amount of about 2% to about 12% by weight based on the total weight of the food or beverage product. In another embodiment, the food or beverage product comprises the sweetener composition in an amount such that the food or beverage product contains allulose, fructose and sucralose in a total amount of about 2% to about 5% by weight based on the total weight of the food or beverage product. In a further embodiment, the food or beverage product comprises the sweetener composition in an amount such that the food or beverage product contains allulose, fructose and sucralose in a total amount of about 4% to about 10% by weight based on the total weight of the food or beverage product. In another embodiment, the food or beverage product comprises the sweetener composition in an amount such that the food or beverage product contains allulose, fructose and sucralose in a total amount of about 6% to about 12% by weight based on the total weight of the food or beverage product.

An alternative aspect of the present invention provides the use of the sweetener composition of the invention in a food product, a beverage product, a pharmaceutical product, a nutritional product, a sports product, or a cosmetic product, as a bulking agent or as a coating agent.

The sweetener composition may be formulated in any ingestible form, for example, as a syrup, in powder form, tablet form, as granules, in a solution or in any other suitable form including beverages and food products.

As outlined in the below example, the sweetener composition of the present invention exhibits an unexpected sucrose equivalent value (SEV) greater than the predicted value based on its individual components. Therefore, the sweetener composition of the present invention displays sweetness synergy.

The following example is exemplary only and is not intended to be limiting in any way.

Example

Demonstration of Sweetness Synergy of the Composition of the Present Invention

Materials and Methods

Round table evaluations were performed with test panelists. Equal sweet 10 SEV concentrations in neutral pH water were made for allulose, fructose and sucralose, as well as a composition comprising allulose, fructose and sucralose. The components of the test compositions are described in the below tables. The mixed compositions were calculated using the Beidler mixture equation for the sweeteners. The Beidler mixture equation for sweeteners is as follows:

$$SEV = \frac{conc \cdot R_{max}}{conc + 1/K}$$

The concentration of each component in the mixture in ppm is divided by SEV (c/R) and is plotted against concentration, c. The slope of the linear regression is the maximum SEV ($R_{max}$). The y-intercept of the linear regression multiplied by $R_{max}$ is the half-maximal sweetness concentration, $1/K$. $R_{max}$ and $1/K$ are the two parameters used in the Beidler equation.

The equal-molar mixture was tested against reference samples for the panelists to determine SEV values. References samples were 4%, 6%, 8%, 10%, 12%, and 14% sucrose in neutral pH water. The test samples were served in 2 ounce (approximately 60 ml) soufflé cups coded with 3-digit codes at room temperature. A two minute wait period between samples was enforced. Water and unsalted crackers was available for the panelists to clear their palates before and during testing. EyeQuestion was used for ballot development and recording of results. Results were collected in EyeQuestion for calculating approximate SEV level of each test sample. The test products analyzed in this experiment are described below in Table 1.

Product Information

TABLE 1

| INGREDIENT | Allulose 10% % | Allulose 10% GRAMS | Sucralose SEV 10 % | Sucralose SEV 10 GRAMS | Fructose SEV 10 % | Fructose SEV 10 GRAMS | Allulose/Fructose/Sucralose % | Allulose/Fructose/Sucralose GRAMS |
|---|---|---|---|---|---|---|---|---|
| Allulose 89% DS syrup | 17.02 | 40.848 | 0 | 0 | 0 | 0 | 5.6733 | 13.616 |
| Sucralose | 0 | 0 | 0.0237 | 0.05688 | 0 | 0 | 0.0079 | 0.01896 |
| Fructose | 0 | 0 | 0 | 0 | 8.55 | 20.52 | 2.85 | 6.84 |
| RO Water | 82.98 | 199.152 | 99.9763 | 240 | 91.45 | 219.48 | 91.468 | 219.525 |
| TOTAL | 100 | 240 | 100 | 240 | 100 | 240 | 100 | 240 |

Results

FIG. 1 illustrates the mean sucrose equivalent values for the sweetener composition of the present invention as well as the SEV for each of the individual components of the sweetener composition.

Table 2 recites the mean and median sucrose equivalent values (SEV) for the sweetener composition of the present invention as well as the SEV for each of the individual components of the sweetener composition.

TABLE 2

|  | Mean 1 | StDev | Median 1 | 1 STDEV |
|---|---|---|---|---|
| Fructose | 10.14286 | 1.214986 | 10 | 0.607493 |
| Sucralose | 9.285714 | 1.112697 | 10 | 0.556349 |
| Allulose | 10.14286 | 1.46385 | 10 | 0.731925 |
| Allulose/ Fructose/ Sucralose | 11.28571 | 1.253566 | 11 | 0.626783 |

|  | Allulose (A) | Sucralose (C) | Fructose (D) | Allulose/ Sucralose/ Fructose (G) |
|---|---|---|---|---|
| Sweetness | 10.14 | 9.29 | 10.14 | 11.29$^{b-c}$ |
| Sweetness | 10.14$^{b-c}$ | 9.29$^{c}$ | 10.14$^{b-c}$ | 11.29$^{a-b}$ |

Level of Significance (Duncan): A' < 99.9%; A < 99,%; a < 95%; a' < 90%
The ANOVA performed is a two-way ANOVA
Level of significance for the grouping (Duncan): 5%

The sweetener composition of the present invention comprising allulose, fructose and sucralose was significantly sweeter than Sucralose at a 95% CI, and significantly sweeter than allulose and Fructose components at a 90% CI. Therefore, the composition of the present invention surprisingly exhibits a sweetness greater than the predicted sweetness based on its individual components

CONCLUSION

The sweetener composition of the present invention exhibits a statistically significant sweetness synergy.

The invention claimed is:

1. A sweetener composition comprising allulose in an amount of about 45% to about 80%, fructose in an amount of about 20% to about 55%, and sucralose in an amount of about 0.01% to about 0.3% by weight relative to the total weight of allulose, fructose and sucralose in the composition.

2. The sweetener composition according to claim 1, comprising allulose in an amount of about 45% to about 80%, fructose in an amount of about 20% to about 55%, and sucralose in an amount of about 0.02% to about 0.3% by weight relative to the total weight of allulose, fructose and sucralose in the composition.

3. The sweetener composition according to claim 1, comprising allulose in an amount of about 55% to about 70%, fructose in an amount of about 30% to about 45%, and sucralose in an amount of about 0.1% to about 0.25% by weight relative to the total weight of allulose, fructose and sucralose in the composition.

4. The sweetener composition according to claim 1, comprising allulose in an amount of about 65% to about 75%, fructose in an amount of about 25% to about 35%, and sucralose in an amount of about 0.01% to about 0.06% by weight relative to the total weight of allulose, fructose and sucralose in the composition.

5. The sweetener composition according to claim 1, comprising allulose in an amount of about 70% to about 80%, fructose in an amount of about 20% to about 30%, and sucralose in an amount of about 0.02% to about 0.1% by weight relative to the total weight of allulose, fructose and sucralose in the composition.

6. The sweetener composition according to claim 1, comprising allulose in an amount of about 45% to about 55%, fructose in an amount of about 45% to about 55%, and sucralose in an amount of about 0.02% to about 0.1% by weight relative to the total weight of allulose, fructose and sucralose in the composition.

7. The sweetener composition according to claim 1, comprising allulose in an amount of about 62%, fructose in an amount of about 38%, and sucralose in an amount of about 0.2% by weight relative to the total weight of allulose, fructose and sucralose in the composition.

8. The sweetener composition according to claim 1, comprising allulose in an amount of about 77%, fructose in an amount of about 23%, and sucralose in an amount of about 0.05% by weight relative to the total weight of allulose, fructose and sucralose in the composition.

9. The sweetener composition according to claim 1, comprising allulose in an amount of about 46%, fructose in an amount of about 54%, and sucralose in an amount of about 0.06% by weight relative to the total weight of allulose, fructose and sucralose in the composition.

10. The sweetener composition according to claim 1, comprising allulose in an amount of about 68%, fructose in an amount of about 32%, and sucralose in an amount of about 0.03% by weight relative to the total weight of allulose, fructose and sucralose in the composition.

11. The sweetener composition according to claim 1, further comprising at least one of a sweet taste improving additive, a bulking agent, a flavoring agent, or a stabilizer.

12. A food or beverage product comprising the sweetener composition according to claim 1.

13. The food or beverage product according to claim 12, wherein the food or beverage product comprises allulose, fructose and sucralose in a total amount of about 2% to about 12% by weight based on the total weight of the food or beverage product.

14. The food or beverage product according to claim 12, wherein the food or beverage product comprises allulose, fructose and sucralose in a total amount of about 2% to about 5% by weight based on the total weight of the food or beverage product.

15. The food or beverage product according to claim 12, wherein the food or beverage product comprises allulose, fructose and sucralose in a total amount of about 4% to about 10% by weight based on the total weight of the food or beverage product.

16. The food or beverage product according to claim 12, wherein the food or beverage product comprises allulose, fructose and sucralose in a total amount of about 6% to about 12% by weight based on the total weight of the food or beverage product.

17. A food or beverage product according to any claim 12, wherein the product is a food product and the sweetener composition is provided as a coating or frosting on the surface of the food product.

18. The food or beverage product according to claim 12, wherein the product is a carbonated or non-carbonated beverage.

19. A table-top sweetener comprising the sweetener composition according to claim 1.

20. A method, comprising using the sweetener composition according to claim 1 in a food product, a beverage product, a pharmaceutical product, a nutritional product, a sports product, or a cosmetic product.

21. A method, comprising using the sweetener composition according to claim 1 as a bulking agent.

22. A method, comprising using the sweetener composition according to claim 1 as a coating agent.

* * * * *